US005434046A

United States Patent [19]

Enns et al.

[11] Patent Number: 5,434,046

[45] Date of Patent: Jul. 18, 1995

[54] DIAGNOSTIC ASSAY BASED ON CIS-PLAIN DRUG RESISTANCE GENE

[75] Inventors: Robert E. Enns, Solano Beach; Stephen B. Howell, Del Mar, both of Calif.

[73] Assignee: The Regents of the University of California, Oakland, Calif.

[21] Appl. No.: 29,328

[22] Filed: Mar. 8, 1993

Related U.S. Application Data

[63] Continuation-in-part of Ser. No. 663,448, Mar. 1, 1991, abandoned.

[51] Int. Cl.[6] ........................ C12Q 1/68; G01N 33/53

[52] U.S. Cl. .......................................... 435/6; 435/7.1

[58] Field of Search ..................................... 435/6, 7.1

[56] References Cited

PUBLICATIONS

P. A. Andrews et al., Cellular Pharmacology of cisplatin: Perspectives on mechanisms of acquired resistance, *Cancer Cells* 235–43 (1990).

P. A. Andrews et al., Rapid emergence of acquired cis–Diamminedichloroplatinum(II) resistance in an in vivo model of human ovarian carcinoma *Cancer Comm.* 2:93–100 (1990).

S. C. Pruitt, Expression vectors permitting cDNA cloning and enrichment for specific sequences by hybridization/selection *Gene* 66:121–134 (1988).

S. Jindal et al., Primary structure of human mitochondrial protein homologous to the bacterial and plant chaperonins and to the 65–kilodalton mycobacterial antigen *Mol. Cell. Biol.* 9:2279–2283 (1989).

W. Hoffmann, Amino acid sequence microheterogeneities of basic (type II) cytokeratins of *Xenopus laevis* epidermis and evolutionary conservativity of helical and non–helical domains *J. Mol. Biol.* 184:713–724 (1985).

S. M. Hemmingsen et al., Homologous plant and bacterial proteins chaperone oligomeric protein assembly *Nature* 333:330–334 (1988).

T. M. Shinnick, The 65–kilodalton antigen of *Mycobacterium tuberculosis. J. Bacteriol.* 169:1080–1088 (1987).

R. E. Enns, Isolation of a gene associated with resistance to cisplatin *Anti–Cancer Drug Des.* 6:340 (1991).

R. E. Enns et al., Isolation and characterization of genes involved in low level cisplatin (DDP) resistance in human ovarian carcinoma cells *Proc. Am. Assoc. Cancer Res. Ann. Meeting* 30:420 (1989).

R. E. Enns et al., an amplified mitochondrial chaperonin gene causes resistance to cisplatin in human ovarian tumor cells *Proc. Am. Assoc. Caner Res.* 32:353 Abstract #2098 (1991).

H. Kimura et al., Regulation of the expression of heat shock protein 60 (HSP60) mRNA in a human ovarian carcinoma cell line *Proc. am. Assoc. Caner Res.* 33:362, Abstract #2161 (1992).

*Primary Examiner*—Richard A. Schwartz
*Assistant Examiner*—Philip W. Carter
*Attorney, Agent, or Firm*—Walter H. Dreger; Jan P. Brunelle

[57] ABSTRACT

This invention relates to DNA encoding drug resistance to cis-platin. The invention also includes expression products of, and vectors and hosts comprising the DNA sequence encoding cis-platin resistance. Also included are immunodiagnostic assays of cis-platin resistance and assays for screening materials having a modulating effect on DNA encoding the cis-platin resistance gene and on the expression product thereof. The invention is further directed to antagonists to the cis-platin resistance gene and the expression product thereof. Recombinant and pharmaceutical means making use of the cis-platin resistance gene and its expression product are also provided.

2 Claims, 6 Drawing Sheets

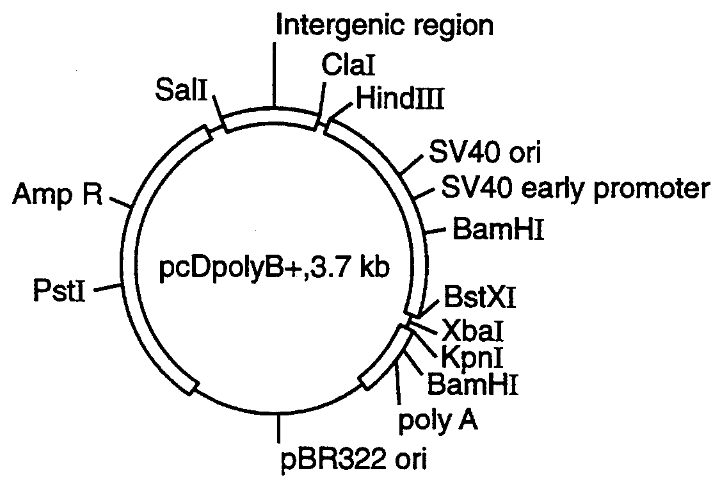
FIG._1A
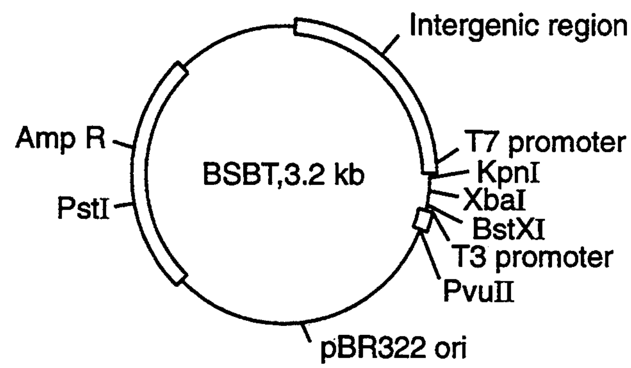
FIG._1B
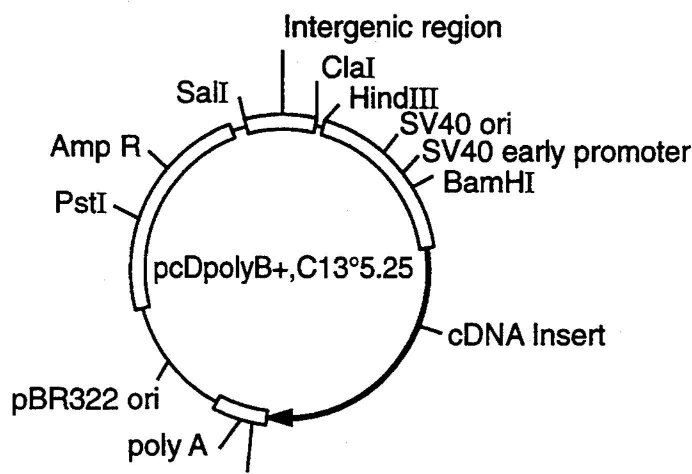
FIG._1C
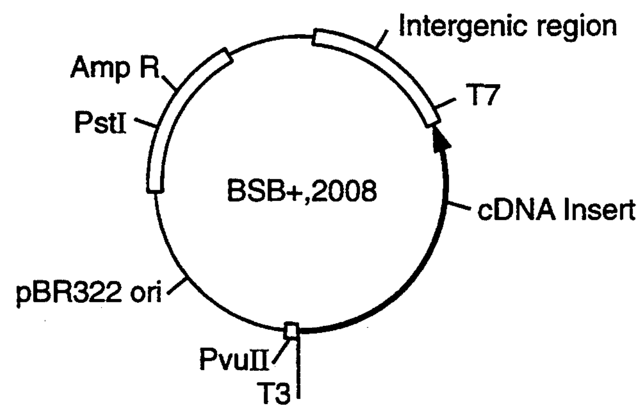
FIG._1D

. . .AGGTCCCGGATCCGGTGGTGGTGCAAATCAAAGAACTGCTCCTCAGTGGATG
TTGCCTTTACTTCTAGGCCTGTACGGAAGTGTTACTTCTGGTCTAAAAGCTGCTG
CAGGGGGTTGTGCCCTCCTTCGATGCATTCCAGCCTTGGACTCATTGACTCCAGC
TAATGAAGATCAAAAAATTGGTATAGAAATTATTAAAAGAACACTCAAAATTCCA
GCA

1429 ATG ACC ATT GCT AAG AAT GCA GGT GTT GAA GGA CCT TTG ATA
476 MET THR ILE ALA LYS ASN ALA GLY VAL GLU GLY PRO LEU ILE

1471 GTT GAG AAA ATT ATG CAA AGT TCC TCA GAA GTT GGT TAT GAT
490 VAL GLU LYS ILE MET GLN SER SER SER GLU VAL GLY TYR ASP

1513 GCT ATG GCT GGA GAT TTT GTG AAT ATG GTG GAA AAA GGA ATC
504 ALA MET ALA GLY ASP PHE VAL ASN MET VAL GLU LYS GLY ILE

1555 ATT GAC CCA ACA AAG GTT GTG AGA ACT GCT TTA TTG GAT GCT
518 ILE ASP PRO THR LYS VAL VAL ARG THR ALA LEU LEU ASP ALA

1597 GCT GGT GTG GCC TCT CTG TTA ACT ACA GCA GAA GTT GTA GTC
532 ALA GLY VAL ALA SER LEU LEU THR THR ALA GLU VAL VAL VAL

1639 ACA GAA ATT CCT AAA GAA GAG AAG GAC CCT GGA ATG GGT GCA
546 THR GLU ILE PRO LYS GLU GLU LYS ASP PRO GLY MET GLY ALA

1681 ATG GGT GGA ATG GGA GGT GGT ATG GGA GGT GGC ATG TTC TAA
560 MET GLY GLY MET GLY GLY GLY MET GLY GLY GLY MET PHE end

1723 CTCCTAGACTAGTGCTTTACCTTTATTAATGAACTGTGACAGGAAGCCCAAGGCA

GTGTTCCTCACCAATAACTTCAGAGAAGTCAGTTGGAGAAAATGAAGAAAAAGGC
TGGCTGAAAATCACTATAACCATCAGTTACTGGTTTCAGTTGACAAAATATATAA
TGGTTTACGTGCTGTCATTGTCCATGCCTACAGATAATTTATTTTGTATTTTTGA
ATAAAAAACATTTGTACATTCCTGATACTGGGTACAAGAGCCATGTACCAGTGTA
CTGCTTTCAACTTAAATCACTGAGGCATTTTTACTACTATTCTGTTAAAATCAGG
ATTTTAGTGCTTGCCACCACCAGATGAGAAGTTAAGCAGCCTTTCTGTGGAGAGT
GAGAATAATTGTGTACAAAGTAGAGAAGTATCCAATTATGTGACAACCTTTGTGT
AATAAAAATTTGTTTAAGTTpolyA. . . .GTACCTTCTGAGGCGGAAAGAACCAG
TGGAAGACTCCGCCT

CGTCGAGGGATCCAGA

FIG._2

```
  1  -----------*->------XXXXXXXXX--XXXXXXXXXXXXXXXXXXX
 51  XX---*>>*------->>***>-------XXXXXXXXXXXXXXX------
101  -*****XXX>>*XX---XXXXXXXXXXXXXXX>***-----XXX-XXXXX
151  XXXXXXX>*--**--XXXXXXXX--****X----XXXXXXXXXXX-----
201  -->>**XXXXXXXXXXXXX>>>>------->>>>>---XXXXXXXXXXXX
251  X--------XXXXXXXXXXX-----XXXXXXXXXXXXXX--X--------
301  --->-*>*XXXXX-----XXX**---XXXXXXXXXXXXXXXX*-X-----
351  XXXXXXXXXXXXXXXXXXXXXXXXXXXXXXXXXXXXXXXXXXXXXXXXXX
401  X------**-XXXXXXXXXXXXXXXXXXXXXXXX---->>----------
451  ---**XXXXXXXXXXXX-XXXXX-X-XXXXX****XXXXXXXXXXX****
501  --X-XXXXXXXXXXXXX-----------XXXXXXXXXXXXXXXXXXXXXX
551  XXXXXXXXX-----******---
```

FIG._3

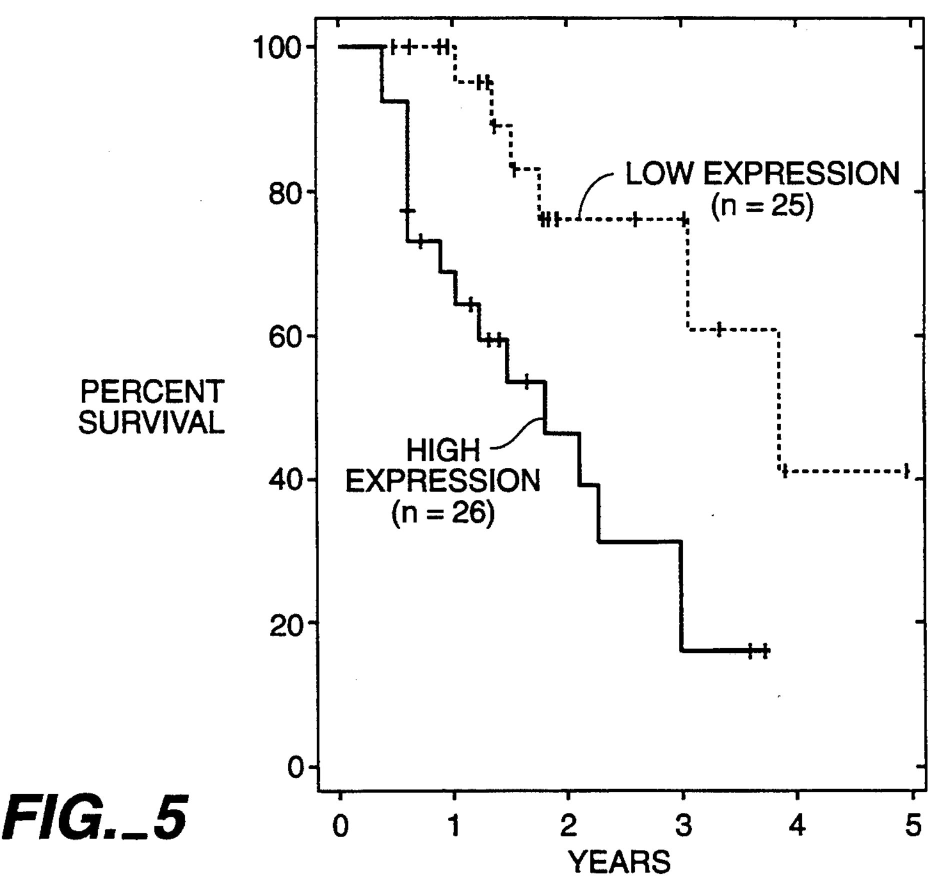

FIG._5

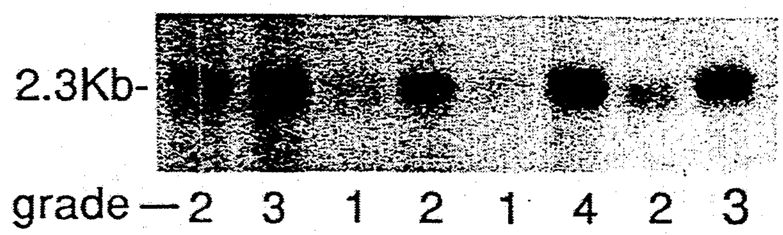
FIG._4A
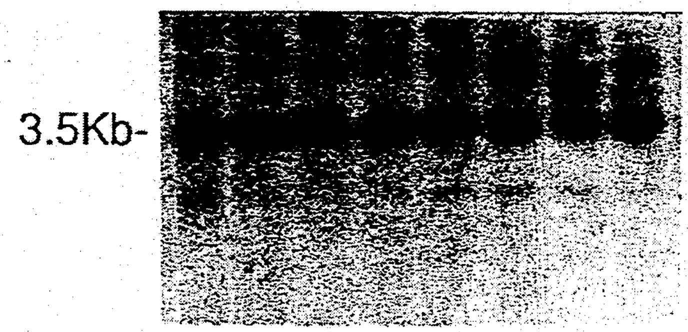
FIG._4B

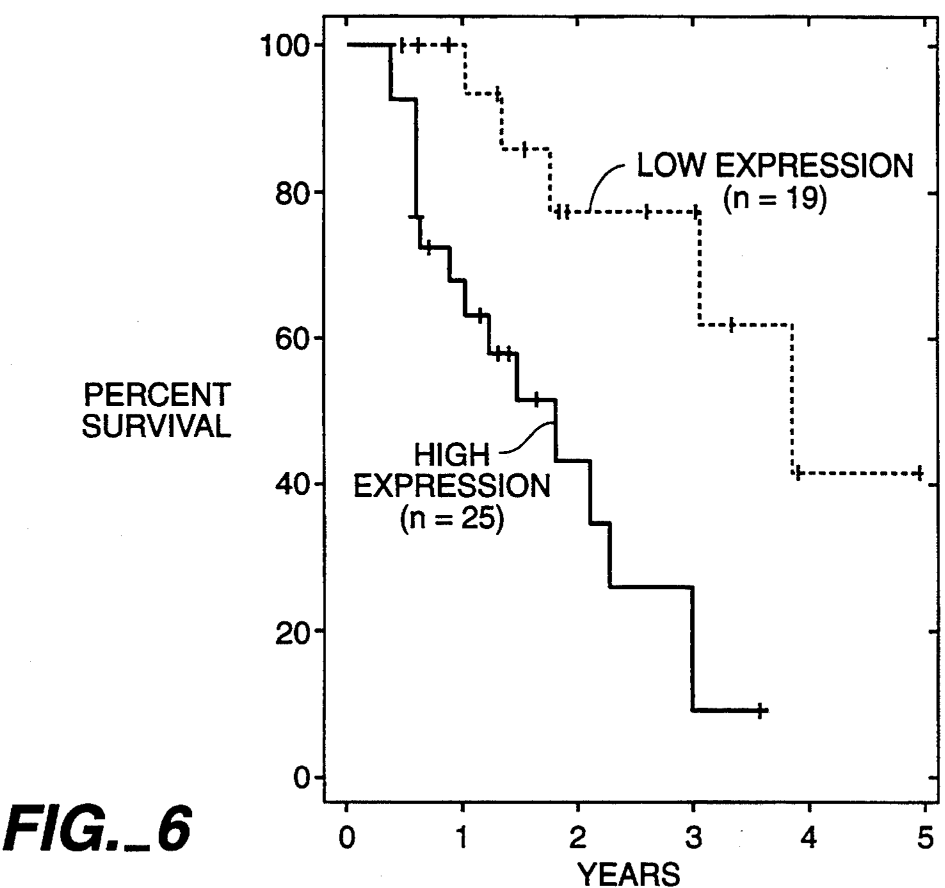
FIG._6
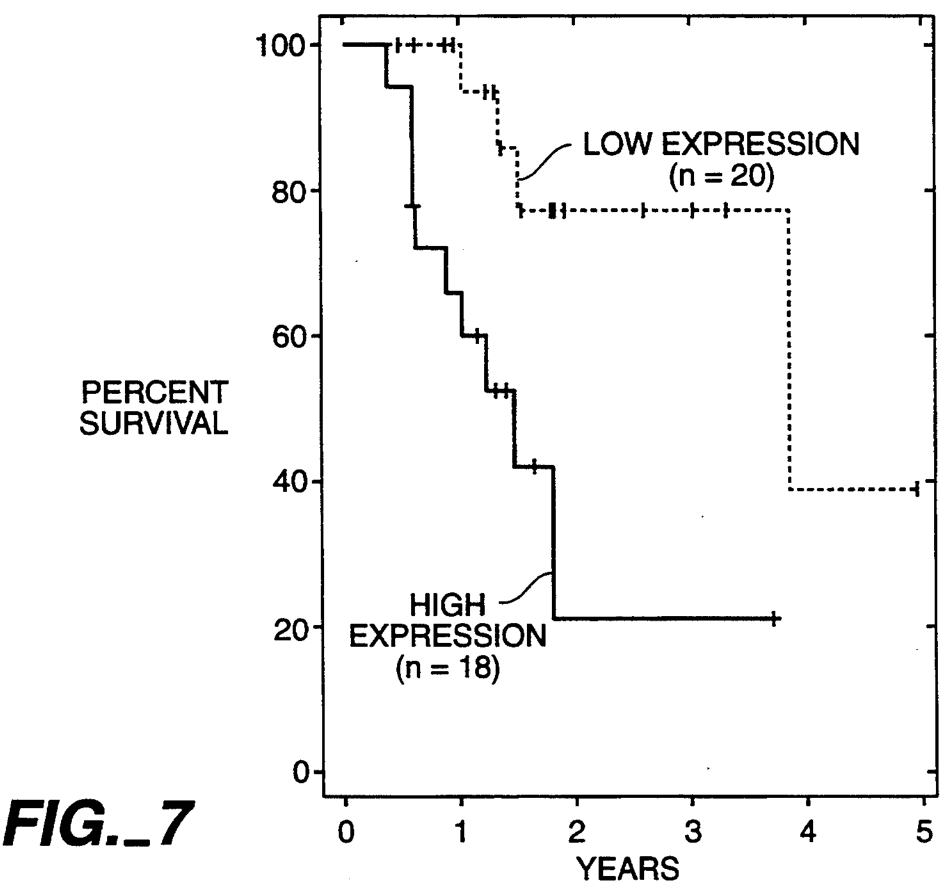
FIG._7

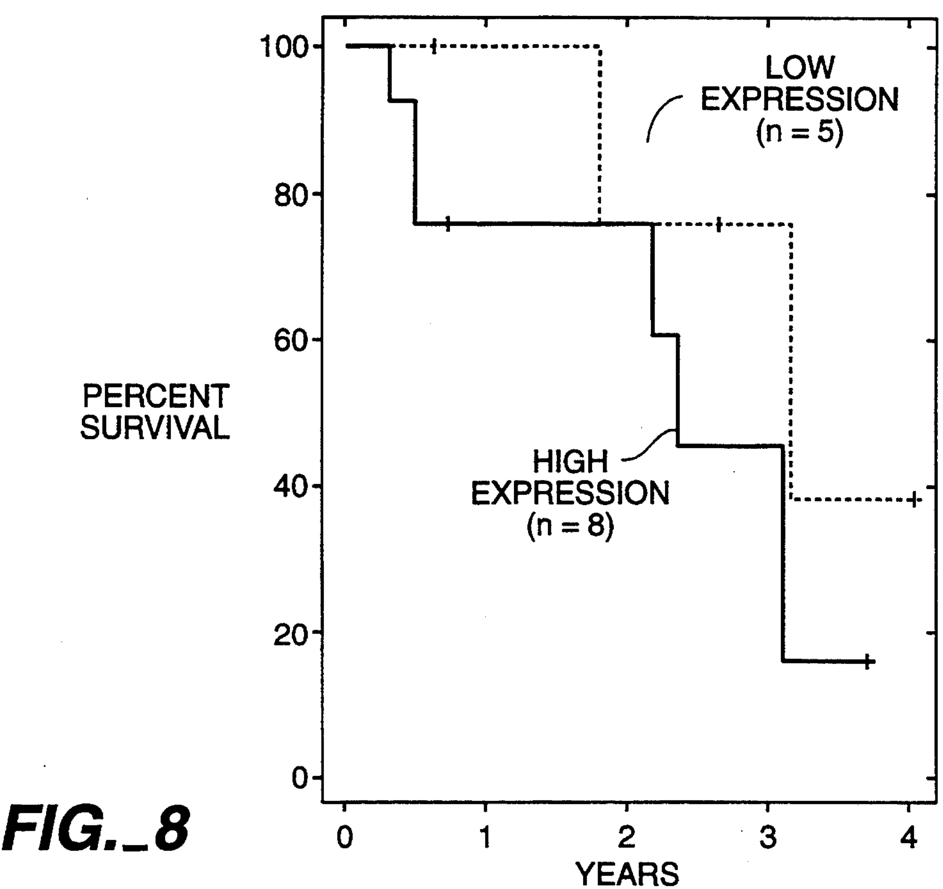
FIG._8
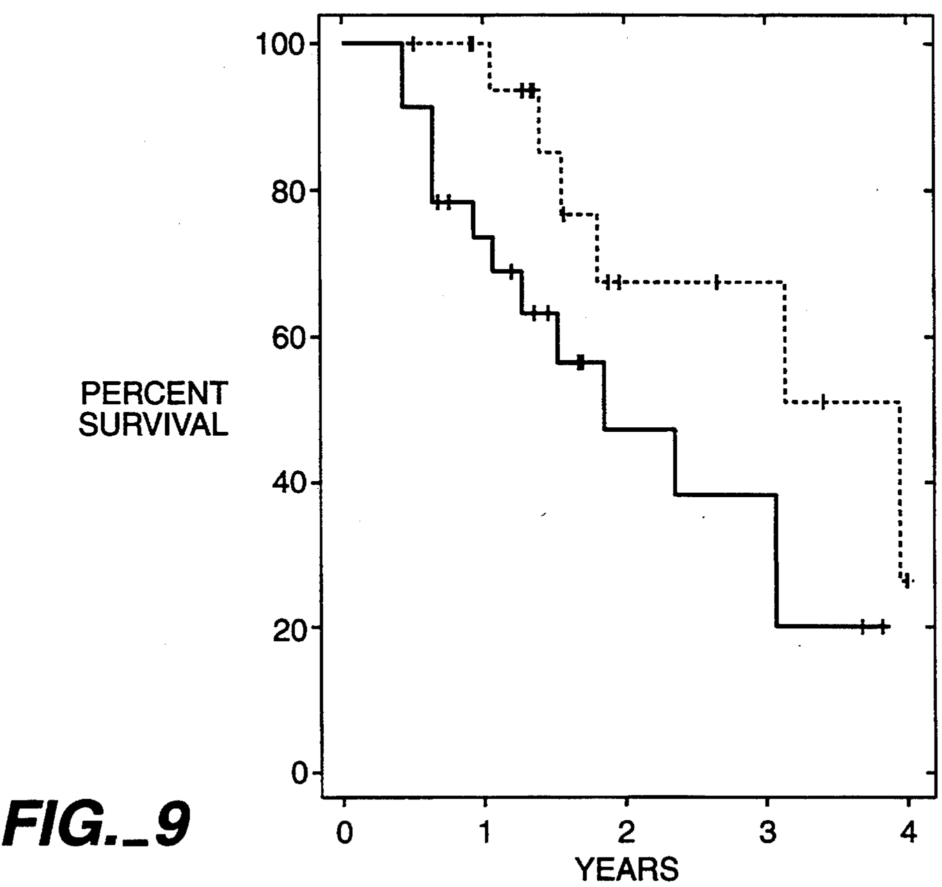
FIG._9

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 1028 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 221..514

( i x ) FEATURE:
( A ) NAME/KEY: miscdifference
( B ) LOCATION: replace(254, "")
( D ) OTHER INFORMATION: /standardname="Single residue change from human chaperonin P1."

-continued

/ note="P1 bp254=T; T4-2 bp254=C; converts Ser ( P 1 ) to Pro (T4-2)."

( i x ) FEATURE:
( A ) NAME/KEY: primerbind
( B ) LOCATION: 989..1003

( i x ) FEATURE:
( A ) NAME/KEY: polyAsite
( B ) LOCATION: 975..986

( i x ) FEATURE:
( A ) NAME/KEY: miscdifference
( B ) LOCATION: replace(1..1028, "")
( D ) OTHER INFORMATION: /standardname="Nucleotide numbering."
/ note="Position 1 in PatentIn =position 1209 in Figure 2."

( x i ) SEQUENCE DESCRIPTION: SEQ ID NO:1:

```
AGGTCCCGGA TCCGGTGGTG GTGCAAATCA AAGAACTGCT CCTCAGTGGA TGTTGCCTTT      60

ACTTCTAGGC CTGTACGGAA GTGTTACTTC TGGTCTAAAA GCTGCTGCAG GGGGTTGTGC     120

CCTCCTTCGA TGCATTCCAG CCTTGGACTC ATTGACTCCA GCTAATGAAG ATCAAAAAAT     180

TGGTATAGAA ATTATTAAAA GAACACTCAA AATTCCAGCA ATG ACC ATT GCT AAG       235
                                            Met Thr Ile Ala Lys
                                              1               5

AAT GCA GGT GTT GAA GGA CCT TTG ATA GTT GAG AAA ATT ATG CAA AGT       283
Asn Ala Gly Val Glu Gly Pro Leu Ile Val Glu Lys Ile Met Gln Ser
                 10                  15                  20

TCC TCA GAA GTT GGT TAT GAT GCT ATG GCT GGA GAT TTT GTG AAT ATG       331
Ser Ser Glu Val Gly Tyr Asp Ala Met Ala Gly Asp Phe Val Asn Met
             25                  30                  35

GTG GAA AAA GGA ATC ATT GAC CCA ACA AAG GTT GTG AGA ACT GCT TTA       379
Val Glu Lys Gly Ile Ile Asp Pro Thr Lys Val Val Arg Thr Ala Leu
         40                  45                  50

TTG GAT GCT GCT GGT GTG GCC TCT CTG TTA ACT ACA GCA GAA GTT GTA       427
Leu Asp Ala Ala Gly Val Ala Ser Leu Leu Thr Thr Ala Glu Val Val
     55                  60                  65

GTC ACA GAA ATT CCT AAA GAA GAG AAG GAC CCT GGA ATG GGT GCA ATG       475
Val Thr Glu Ile Pro Lys Glu Glu Lys Asp Pro Gly Met Gly Ala Met
 70                  75                  80                  85

GGT GGA ATG GGA GGT GGT ATG GGA GGT GGC ATG TTC TAACTCCTAG            521
Gly Gly Met Gly Gly Gly Met Gly Gly Gly Met Phe
                 90                  95

ACTAGTGCTT TACCTTTATT AATGAACTGT GACAGGAAGC CCAAGGCAGT GTTCCTCACC     581

AATAACTTCA GAGAAGTCAG TTGGAGAAAA TGAAGAAAAA GGCTGGCTGA AAATCACTAT     641

AACCATCAGT TACTGGTTTC AGTTGACAAA ATATATAATG GTTTACGTGC TGTCATTGTC     701

CATGCCTACA GATAATTTAT TTTGTATTTT TGAATAAAAA ACATTTGTAC ATTCCTGATA     761

CTGGGTACAA GAGCCATGTA CCAGTGTACT GCTTTCAACT TAAATCACTG AGGCATTTTT     821

ACTACTATTC TGTTAAAATC AGGATTTTAG TGCTTGCCAC CACCAGATGA GAAGTTAAGC     881

AGCCTTTCTG TGGAGAGTGA GAATAATTGT GTACAAAGTA GAGAAGTATC CAATTATGTG     941

ACAACCTTTG TGTAATAAAA ATTTGTTTAA GTTAAAAAAA AAAAAGTACC TTCTGAGGCG    1001

GAAAGAACCA GCGTCGAGGG ATCCAGA                                        1028
```

( 2 ) INFORMATION FOR SEQ ID NO:2:

( i ) SEQUENCE CHARACTERISTICS:
( A ) LENGTH: 97 amino acids
( B ) TYPE: amino acid
( D ) TOPOLOGY: linear ( i i ) MOLECULE TYPE: protein -continued ( x i ) SEQUENCE DESCRIPTION: SEQ ID NO:2:

```
Met Thr Ile Ala Lys Asn Ala Gly Val Glu Gly Pro Leu Ile Val Glu
 1               5                   10                  15

Lys Ile Met Gln Ser Ser Ser Glu Val Gly Tyr Asp Ala Met Ala Gly
            20                  25                  30

Asp Phe Val Asn Met Val Glu Lys Gly Ile Ile Asp Pro Thr Lys Val
        35                  40                  45

Val Arg Thr Ala Leu Leu Asp Ala Ala Gly Val Ala Ser Leu Leu Thr
    50                  55                  60

Thr Ala Glu Val Val Val Thr Glu Ile Pro Lys Glu Glu Lys Asp Pro
65                  70                  75                  80

Gly Met Gly Ala Met Gly Gly Met Gly Gly Gly Met Gly Gly Gly Met
                85                  90                  95

Phe
```

DIAGNOSTIC ASSAY BASED ON CIS-PLAIN DRUG RESISTANCE GENE

CROSS REFERENCE TO RELATED APPLICATIONS

This is a continuation-in-part application of application U.S. Ser. No. 07/663,448, filed 01 Mar. 1991 now abandoned.

FIELD OF THE INVENTION

The present invention is based upon the identification of a gene for drug resistance to cis-platin. The DNA encoding the functional domain for drug resistance to cis-platin is defined along with its expression product. This information is utilized for purposes of designing assays for testing drug candidates that would modulate its activity and otherwise provide for exploitation for purposes of reducing the effects of drug resistance to the use of cis-platin in cancer therapy.

BACKGROUND OF THE INVENTION

Cis-platin (DDP) is one of the most widely used antineoplastic agents for the treatment of human cancer with activity against a broad spectrum of malignancies, including testicular, ovarian, head and neck, bladder, and some forms of lung cancer. In spite of its potency, the frequent development of resistance to this drug is proving to be a major obstacle to curative therapy.(1) DDP resistance is expressed co-dominantly and is phenotypically stable for long periods in the absence of selection.(2) Unlike cells selected with many antimetabolites and drugs that participate in the multiple drug resistance phenotype mediated by the MDR I gene(3), both in vitro and in vivo selection with DDP at clinically relevant intensities usually results in cells that are only two- to four-fold resistant to this drug.(4) The molecular basis of DDP resistance has not heretofore been understood. Factors that have been identified as capable of contributing to DDP resistance include diminished DDP uptake, elevated glutathionine or metallothioneins and enhanced repair of DDP-induced DNA adducts(2).

It is an object of the present invention to identify the gene or genes involved in the DDP-resistant phenotype. Once identified, it would be possible to exploit this information in the development of assays, and so forth, based upon knowledge of the identification and characterization of the expression product of that gene.

SUMMARY OF THE INVENTION

The predicate of the present invention is based upon the identification and characterization herein of the gene encoding the drug resistance expression product of cis-platin (DDP). The present invention provides the DNA sequence encoding that expression product, and is directed in all respects to the various recombinant aspects whereby that DNA sequence is harnessed for producing the expression product via expression vectors in transfected hosts. The invention also embraces various assays based upon the knowledge and characterization of that expression product providing immuno-diagnostic assays for cis-platin drug resistance, methods of screening for extrinsic materials that are capable of modulating the drug resistance and the development of antagonists to the gene and/or its expression product such that cis-platin drug resistance can be reduced or eliminated with effectual administration of cis-platin to the tumor patient.

The present invention is thus directed to:

1) The DNA sequence encoding the drug resistant gene for cis-platin or fragments thereof and to DNA sequences encoding bioequivalent expression products for drug resistance to cis-platin,
2) Recombinant expression vectors operatively harboring the DNA of 1),
3) Recombinant hosts operatively transfected with the expression vectors of 2),
4) The expression product of the DNA of 1),
5) Processes for the preparation of the products 4),
6) Immunodiagnostic assays based upon the identification and characterization of the expression products 4),
7) Assays useful for screening extrinsic materials having a modulating effect on the DNA 1) or product 4),
8) Antagonists capable of interfering with the DNA 1) or product 4) so as to render them biologically ineffectual, and
9) Recombinant/pharmaceutical means for effecting the present invention in the commercial sector.

BRIEF DESCRIPTION OF THE DRAWINGS

FIGS. **1*a* to 1*d*** depict expression vectors capable of producing an expression product for the drug resistance gene of DDP.

FIG. 2 sets forth the DNA and amino acid sequence for a fragment of the DDP drug-resistant gene (SEQ ID NO:1).

FIG. 3 depicts the secondary structure of human P1 mitochondrial chaperonin polypeptide. Shading indicates the 97 amino acid portion predicted from the insert recovered from clones T4-1 and 2 and that corresponds to the sequence set forth in FIG. 2 (SEQ ID NO:1).

FIG. **4*a*** is an example of Northern blot analyses. The mRNA expression of HSP-60 showed large differences, grade 1 to grade 4.

FIG. **4*b*** is an example of Southern blot analyses of DNA digested by EcoR I. The results show no evidence of gene amplification or rearrangement.

FIG. 5 shows overall survival of 25 patients with low HSP-60 expression ( - - - ) and 26 patients with high expression (_). The curves differ with a p value of 0.0018.

FIG. 6 shows overall survival of patients with FIGO stage III; (- - -) 19 patients with low HSP-60 expression; (_) 25 patients with high HSP-60 expression; $p=0.0013$.

FIG. 7 shows overall survival of patients without prior chemotherapy; (- - -) 20 patients with low HSP-60 expression; (_) 18 patients with high HSP-60 expression; $p=0.0040$.

FIG. 8 shows overall survival of patients with prior chemotherapy measured from date of diagnosis; (- - -) 5 patients with low HSP-60 expression; (_) 8 patients with high HSP-60 expression; $p=0.243$.

FIG. 9 shows overall survival of patients with documented grade 2 or 3 ovarian carcinomas; (- - -) 18 patients with low HSP-60 expression; (_) 23 patients with high HSP-60 expression; $p=0.0444$.

DETAILED DESCRIPTION

Definitions

By the term "recombinant DNA molecule" or "rDNA molecule" herein is meant a molecule that has been produced as a discreet entity away from associated presence in the genome of an individual. As such, it is an entity that is an isolate from the environment in which it is ordinarily found, and therefore, capable of producing novel utility for the extrinsic preparation of its expression product.

The term "biofunctional equivalent or derivative" or grammatical equivalents herein is used to provide a functional definition for those entities that have, or can be expected to have, that biological function/utility of that more precise expression product species set forth explicitly in FIG. 2 (SEQ ID NO:1) as the DDP drug-resistant gene/expression product. Having demonstrated herein the functional domain of the DDP expression product and its gene, one can produce extrinsically other DNA products encoding that functional domain and having other variations, such as different amino acids, truncation, and variants having differences such as glycosylation folding, and so forth. All such entities, on a DNA or amino acid expression product level, that function equivalently to the expression product of the DDP drug- resistant gene as depicted in FIG. 2 (SEQ ID NO:1), are included within the scope of this term.

By the term "modulating effect" or grammatical equivalents herein is meant both active and passive impact on the DDP drug-resistant gene/expression product. These include, but shall not be construed as limited to, blocking the effect of the function of the DDP drug-resistant gene/expression product or by decreasing its functionality.

Preferred Embodiment and Extrapolations

The present invention is based upon the identification and characterization of the DDP drug-resistant gene and its expression product. Those characteristics are set forth herein by detailing the DNA and deduced amino acid sequence of at least the biofunctional portion of that gene.

Protocol is available for the production of operative expression vectors harboring that DNA or bioequivalents thereof, by ligating to 3- and 5- flanking regions that supply the DNA elements necessary for the two-part components of expression, transcription and translation. Extant literature provides details for proper construction of such vectors using means generally well known in the art. Reference for but one example is made to Maniatis, et al. *Molecular Cloning: A Laboratory Manual,* Cold Spring Harbor Laboratory, New York, 1982, and various subsequent editions thereof.

Various hosts for the transfecting DNA described above are available in the art. For example, various cultures are available via the American Type Culture Collection and other public depositories. For example, a useful prokaryote system could employ vector pKC30 (Shimatake et al., *Nature* 292, 128 (1981) or vector pKK177-3 (Amann et al., *Gene* 40, 183 (1985). A useful eukaryote system could employ vector pMAMneo blue (available publicly from Clonetech, Inc., Palo Alto, Calif.) or an Okayama-Berg vector (*Mol. & Cell. Biol.* p. 161 (February 1982) or p. 280 (February 1983)).

The foregoing description and following experimental details set forth the methodology employed initially by the present researchers in identifying and providing the DNA encoding the functional portion of the DDP drug-resistant gene. The art skilled will recognize that by supplying that information, and the characterization and use of that information as detailed herein, it is not necessary, or perhaps even scientifically advisable, to repeat these details in their endeavors to reproduce this work. Instead, they may choose to employ alternative, reliable and known methods. Thus, they may identify the potential of related or bioequivalent polypeptide expression products via immuno- cross-reactivity methods. They may synthesize the underlying DNA sequence for deployment within various suitable operative expression vectors and culture systems. They may use the sequence herein supplied to make probes, to screen genomic libraries and isolate total encoding DNA for deployment as described herein. They may use the sequence information herein in cross-hybridization procedures to isolate, characterize and deploy as above described DNA encoding DDP drug-resistance gene of other species, or DNA encoding related DDP drug-resistant genes of the same or other species, or to devise DNA for such characterization, use and deployment encoding functionally equivalent materials of all of the above, differing in various ways from the wild type species, or its functional domain.

The art skilled may also employ alternative methods specifically exploiting that information in the design and development of various assays from which one can measure DDP drug resistance from the tumor cells of test individuals and to assay for and identify extrinsic materials that modulate the activity of the DDP drug resistance gene and/or its expression product. Once identified, those extrinsic materials can be compounded into a form suitable for pharmaceutical compositions that can be administered via methodology generally well known in the art.

EXAMPLE 1

Preparation of a Library Enriched in Sequences Over-expressed in DDP-resistant Cells We sought to identify genes involved in the DDP-resistant phenotype by isolating sequences over-expressed in human ovarian carcinoma cells selected for resistance to DDP in vitro. The subtractive hybridization technique we used was based on the construction of a variant of the Okayama-Berg cDNA libraries (5) from both the DDP sensitive human ovarian carcinoma cell line 2008 (4) and a variant, C13*5.25 (5), selected for 10-fold resistance by repeated in vitro exposure to DDP (6). A library from the 2008 cells was constructed in BSB+ (5), and a library from the C13*5.25 cells was constructed in the vector pcDpolyB+ (5), both of which can be prepared as a single stranded DNA.

FIG. 1 shows schematic diagrams of the pcDpolyB+ and BSB+ expression systems (5) and the single stranded C13*5.25 and 2008 cDNA libraries constructed with these vectors. The vectors were restricted with KpnI, oligo(dT) tailed, restricted with XbaI to remove unwanted opposite strand tailing, and gel purified. Ten ug of poly(A)+ RNA were added to 2 ug of vector, annealed, and oligo(dC) tailed. The plasmids were digested with BstXI to remove unwanted opposite strand dC tailing; this was followed by ligation with T4 ligase, treatment with RNAse H to remove the original message, and second strand cDNA synthesis with DNA polymerase I. After amplifying the *E. coli* strain XL1 blue with helper phage R408 (Stratagene), grown overnight, and single-stranded phage collected for substraction. Twenty-five ug of the BSB+ 2008 library were attached to Cn-Br sepharose beads which were then annealed with 5 ug of the pcDpolyB+ C13*5.25 library. It is important to note that all the vector sequences that were common between the two libraries were like-stranded; thus annealing was anticipated only between homologous cDNA inserts. Any amplified or unique single-stranded pcDpolyB+ C13*5.25 library inserts (as well as any pcDpolyB+ vector molecules lacking inserts) were subsequently eluted on a bullet column, transfected into DH5 for amplification, and then used to co-transfect DDP-sensitive hamster DG44 cells.

While the vector sequences are in the same orientation in the two libraries, the inserts are in the opposite orientation (FIG. 1). Thus, when single stranded copies of the two libraries are hybridized, the cDNA inserts representing mRNA expressed in both types of cells form double stranded hybrids, whereas cDNAs from transcripts expressed uniquely in one or the other cell remain single stranded. The single stranded pcDpolyB+ library prepared from the C13*5.25 cells was subtracted against a 5-fold excess of the single stranded 2008 BSB+ library previously bound to activated Cn-Br beads. The unbound circular molecules were eluted and transfected directly into *E. coli* strain DH5 (publicly available).

The resulting sublibrary was thus enriched in sequence over- or uniquely expressed in C13*5.25 cells. This was co-transfected with pSV2-neo (ATCC Accession No. 37149) into DDP-sensitive Chinese hamster ovary hamster cells that were selected first with G418 and then 5 uM DDP (28 times the $IC_{50}$). This procedure yielded a total of 24 clones of which 7 (T4-1 through 7) were found to be DDP-resistant when retested for sensitivity to DDP in a clonogenic assay; the $IC_{50}$ values for these 7 clones ranged from 2.3–6.1-fold higher than the value of 0.18 uM for the untransfected DG44 cells.

EXAMPLE 2

Determination of the Nucleic Acid Sequence Over-expressed in DDP-resistant Cells DG44 CELLS (19) were co-transfected with 1 ug pSV2-neo and 10 ug enriched library per plate, and selected with 0.58 mM G418 for 7 days starting 2 days after transfection. The resulting colonies were combined, grown to mass culture and treated with 5 uM DDP for 7 days. Surviving colonies were plucked individually, retested for resistance to DDP in a clonogenic assay, and PCR was carried out on the boiled and proteinase K-treated lysate from one hundred cells.

PCR primers were synthesized corresponding to Okayama-Berg vector sequences just 5′ and 3′ to the insert site (FIG. 2) (SEQ ID NO:1), and polymerase chain reaction (PCR) was performed using genomic DNA from each of the 7 DDP-resistant clones. All 7 clones yielded a product of 1.0 kb; the PCR product from clone T4-2 was blunt-end ligated into the EcoRV site of Bluescript and sequenced using a series of synthetic oligonucleotides.

FIG. 2 (SEQ ID NO:1) shows the sequence of the P1 cDNA recovered by PCR from DDP-sensitive hamster DG44 cells co-transfected with pSV2-neo and the pcDpolyB+ C13*5.25 library enriched by subtraction against a BSB+ made from 2008 cells. The vector sequences are indicated by shading, and the sequence of the PCR primers used to recover the insert is shown in bold lettering. The BamH1 sites within the vector sequences 5′ and 3′ to the insert used to obtain a probe for Northern blotting are indicated by underlined bold lettering. The single base differences from the previously reported human P1 cDNA at position 1462 is shaded. A polyadenylation signal sequence is present starting 20 bases 5′ from the polyA tail.

FIG. 2 (SEQ ID NO:1) shows that the nucleotide sequence of the non-vector portion of the PCR product from T4-2 differs from that reported for the carboxyl terminal portion of the human chaperonin P1 (7) by only a single nucleotide. P1 is a 573 amino acid protein containing a mitochondria leader sequence (7) that by immunofluorescence and mitochondrial subfractionation localizes to the mitochondrial matrix (8). The change from a T in the P1 sequence to a C in the clone T4-2 sequence at position 1462 results in conversion of the serine at amino acid position 488 in the P1 sequence to a proline in the T4-2 sequence. To determine whether this single nucleotide difference resulted from a Taq polymerase error, the 1.0 kb PCR product obtained from clone T4-1 was also sequenced as was found to contain the same nucleotide difference. However, sequencing of several clones isolated from a subtraction performed between 2008 and C8, a 2–3 fold DDP-resistant variant of 2008 isolated at an earlier stage during the selection of C13*5.25, disclosed that one of these also contained the same carboxyl terminal portion of P1 as had been recovered by PCR from the T4-1 and T4-2 clones. This sequence, however, did not contain an altered base at position 1462. Thus, this mutation was not abundantly represented during the early phase of DDP resistance development, but appeared at some point during the additional rounds of DDP selection.

A 1.1 kb BamHI fragment including the entire T4-2 sequence was used to probe Northern blots of total RNA from 2008 cells, a 2–3-fold DDP resistant C8 cells, and 10-fold DDP resistant C13*5.25 cells. In all 3 types of cells, the probe detected a message of approximately 2.1 kb. Previously, a probe for human P1 was reported to detect a mRNA of approximately 2.3 kb (7). When normalized to the extent of hybridization with beta actin by densitometric scanning, expression of the P1 message was increased by only 2-fold in both the C8 and the C13*5.25 cells relative to the 2008 cells.

The DDP-resistant T4-2 clone contains, in the transfected plasmid, P1 sequence that could code for only a 134 amino acid portion of the protein consisting of amino acid 440 to 573 of the carboxyl terminal end. FIG. 2 (SEQ ID NO:1) shows that if translation starts at the first methionine 3′ to the Okayama-Berg sequence that is not followed shortly thereafter by a stop codon, one would anticipate translation of a protein with a $M_r$ of 9837 representing only the carboxyl-terminal 97 amino acids of the P1 protein. Since this protein lacks the mitochondrial leader sequence of P1, it would be expected to remain cytoplasmic. This portion of the protein contains the repeating $(GLY)_{3-4}$MET motif that is characteristic of cytokeratins (9) and constitutes a major coiled portion of the P1 protein (FIG. 3).

Mitochondrial P1 is an abundant cellular protein with extensive homology to the chaperonin family of proteins, including the GroEL protein of *E. coli* (10), the 65-kDa major antigen of mycobacteria (11), and the "rubisco" large subunit-binding protein of plant chloroplasts (10). Chaperonins are postulated (10,12) to transiently associate with a variety of other proteins to facilitate folding an acquisition of oligomeric structure. They share a number of common features (10) including inducibility by heat shock, homo-oligomer structure of 7 or 14 subunits, relatively high abundance, and weak ATPase activity. P1 has been reported to exist as a homo-oligomer of 7 subunits (7), and the hamster homolog of P1 has been reported to have ATPase activity (13).

How expression of the carboxyl terminal portion of P1 causes DDP resistance is unclear. Expression of P1 mRNA was only minimally elevated in the DDP-resistant C8 and C13*5.25 cells, however, resistance in these cells probably involves multiple mechanisms. Nevertheless, C13*5.25 cells have been reported to have abnormal mitochondria on electron microscopy, an elevated mitochondrial potential, and 15 and 29-fold hypersensitivity respectively to the two cationic agents that localize to mitochondria, tetraphenylphosphonium and rhodamine 123 (14). The carboxyl-terminal portion of P1 is extraordinarily rich in methionine, containing 5 methionines in a stretch of 15 amino acid. Since P1 exists as a homomultimer of 7 units (7), a total of 35 methionine may be regionally grouped in the active form of the protein. DDP is known to react readily and selectively with the active site methionine of the $alpha_2$ macroglobulin and the $alpha_1$ (formerly $alpha_1$-antitrypsin) proteinase inhibitors (15,16), and render $alpha_2$ macroglobulin unable to bind to its macrophage reactor by inactivating an adjacent methionine (17). It also cross-links adjacent monomers (15). Relatively small increases in the cellular level of the metallothioneins, another group of proteins known to complex with DDP, has been reported to cause resistance to DDP (18). We propose that over-expression of P1, or its carboxyl terminal portion, results in the extra-nuclear trapping of DDP thereby decreasing DNA adduct formation and cytotoxicity. Either over-expression or the serine to proline mutation may alter the chaperonin function of the mitochondrial protein. It remains possible that reaction with P1 in sensitive cells contributes to the cytotoxicity of DDP.

EXAMPLE 3

Correlation of the Survival of Ovarian Cancer Patients with mRNA Expression of the Cis-platin Resistance Gene There is marked heterogeneity in the expression of HSP-60 mRNA, both between normal tissues in the adult and fetus, and between tumor samples of the same histologic type (50). This is especially true in ovarian cancers. This study evaluated the independent prognostic significance of HSP-60 expression in ovarian tumors, for which clinical follow-up (median, 17 months) was available.

Materials and Methods

1. DNA and RNA Samples

Frozen ovarian cancer tissues from surgical specimen obtained at the Memorial Sloan-Kettering Cancer Center were used for this study. The tissues were quick frozen and stored in airtight, sealed plastic tubes at −70° C. Fifty-one patients with FIGO stage I–IV ovarian cancer were entered on study. All patients were treated with debulking surgery and chemotherapy including cisplatin or carboplatin. Of the 51 patients, 38 patients had no prior chemotherapy at the time of sampling and 13 patients had prior chemotherapy including cisplatin or carboplatin.

Tumor tissues were fractured in liquid nitrogen to obtain a representative tissue sample suitable for DNA and RNA preparation. Each tumor sample (300–500 mg) was ground to powder in liquid nitrogen with a mortar and pestle. The tissue powder was extracted for DNA and RNA simultaneously by homogenization in guanidine thiocyanate and precipitation in guanidine hydrochloride and ethanol as previously described (33, 34, 35). All analyses were done in a blinded fashion, i.e., each assay was conducted independently and blinded with respect to the results of other assays or clinical information. This was done to circumvent the possibility of introducing bias in evaluation of any case based on prior knowledge of results from another test.

2. Northern Hybridization Identification of a messenger encoding the HSP-60 protein was done by Northern blot hybridization of total RNA extracted from epithelial ovarian cancer tissues. Adjacent normal ovarian tissue from the same patient was used as control. Fifteen μg of total RNA were denatured and loaded onto 1.0% agarose gels containing formaldehyde, separated by electrophoresis, and transferred onto nylon filter papers (36, 37). All filters were baked in a vacuum oven for 2 hours at 80° C., prehybridized in 1M NaCl containing 50% formamide, 10% dextran sulfate, 1.0% SDS, and denatured salmon sperm DNA (100 μg/ml) for at least 1 hour, then hybridized in the same solution containing $^{32}$P-labeled HSP-60 probe with specific activity of $1\times10$ cpm per μg of DNA, cDNA of the 0.89 Kb carboxyl-terminal portion of human HSP-60 was prepared and used as a probe. The probe was labeled by using the random primer extension method. Hybridization occurred at 42° C. for 21 hours, followed by washing of the filter under the following conditions in succession: $2\times$SSC for 20 minutes at room temperature; two washes of 20 minutes each in $2\times$SSC, 0.1& SDS at 65° C.; one wash of 30 minutes in 0.5 SSC, 0.1% SDS at 65° C. Filters were then exposed to XAR-5 x-ray film (Kodak) for autoradiography. Northern blots were semiquantitatively scored for HSP-60 mRNA by the use of both direct visualization and densitometry. The level of HSP-60 expression in each tumor sample was normalized relative to the HSP-60 mRNA expression levels in control adjacent normal ovarian tissue. HSP-60 mRNA expression in tumors showing the same, twice, three times and four times the HSP-mRNA band intensity as controls was respectively graded 1, 2, 3 and 4.

3. Southern Hybridization

DNA was digested with EcoR I as described (39). A total of 12 μg of EcoR I-digested DNA was loaded onto 0.8% agarose gels, separated by electrophoresis, and transferred onto nylon filters (36, 39). All filters were treated the same way as described for Northern hybridization.

4. Statistical Methods

The level of HSP-60 mRNA expression was graded 1 (lowest) to 4 (highest). Patients with grade 1 or 2 HSP-60 expression were combined into a low expression group, and patients with grade 3 or 4 expression were combined into a high expression group.

Comparisons of categorical variables between the low expression group and the high expression group were performed with the Monte Carlo $2\times C$ contingency table test (40). Comparisons of dichotomous variables were performed by Fisher's exact test. Comparisons of age were performed by the Mann-Whitney test.

Survival was assessed from the date of diagnosis to death or last contact. The prognostic importance of several variables with respect to survival was assessed using both univariate and multivariate Cox proportional hazards modeling (41). Statistical significance in univariate and multivarite models were determined by a likelihood ratio (LR) test (42). Estimates of survival probabilities were calculated by the method of Kaplan-Meier (43) and the curves were statistically examined by Mantel-Haenszel test (44). Unless otherwise specified, all P values were two-sided, and significance was at the level of $p<0.05$.

Results

HSP-60 mRNA expression was quantitated by Northern blot analysis (FIG. 4). The message was 2.3 Kb and was a little smaller than the $\beta$ actin message. Of the 51 patients, 10 cases were classified as grade 1, 15 cases as grade 2, 17 cases as grade 3, and 9 cases as grade 4 with regard to the levels of HSP-60 expression. The 25 cases included in grade 1 or 2 were combined into the low expression group and the 26 cases included in grade 3 or 4 were combined into the high expression group (Table 1).

TABLE 1

| | The level of HSP-60 mRNA expression | | | |
|---|---|---|---|---|
| Level of expression | HSP-60 grade | Number of patients without prior chemotherapy | Number of patients with prior chemotherapy | Total |
| Low | 1 | 8 | 2 | 10 |
| | 2 | 12 | 3 | 15 |
| High | 3 | 11 | 6 | 17 |

TABLE 1-continued

| | The level of HSP-60 mRNA expression | | | |
|---|---|---|---|---|
| Level of expression | HSP-60 grade | Number of patients without prior chemotherapy | Number of patients with prior chemotherapy | Total |
| | 4 | 7 | 2 | 9 |
| Total | | 38 | 13 | 51 |

The characteristics of patients in the low and high expression groups are shown in Table 2. No significant differences were observed between these groups with regard to age, cell type, pathologic grade, FIGO stage and prior chemotherapy ($p>0.05$), although there were 4 grade 1 tumors in the low expression group and none in the high expression group. Forty-four of the 51 patients (86%) had stage III tumors and 32 patients (63%) had pathologic grade 3. Thirty-eight patients (75%) had no prior chemotherapy at the time of biopsy.

TABLE 2

| | Patient Characteristics HSP-60 mRNA expression | | |
|---|---|---|---|
| | Low expression group | High expression group | p-value |
| Patients examined | 25 | 26 | |
| Median age, years (range) | 63.5 (39–79) | 62 (34–77) | 0.398 |
| Median follow up, months (range) | 21.6 (4.7–60.8) | 14.3 (4.3–45.7) | |
| Cell type | | | 0.741 |
| Serous | 6 | 4 | |
| Mucinous | 3 | 1 | |
| Endometrioid | 3 | 2 | |
| Clear cell carcinoma | 1 | 1 | |
| Adenocarcinoma, unspecified | 12 | 18 | |
| Pathologic grade* | | | 0.057 |
| 1 | 4 | 0 | |
| 2 | 5 | 4 | |
| 3 | 13 | 19 | |
| unknown | 3 | 3 | |
| FIGO stage | | | 0.131 |
| I | 3 | 1 | |
| II | 1 | 0 | |
| III | 19 | 25 | |
| IV | 2 | 0 | |
| Prior chemotherapy | | | 0.523 |
| (−) | 20 | 18 | |
| (+) | 5 | 8 | |

*Pathologic grade category "unknown" omitted from analysis

Univariate Analysis of Survival Time

Univariate analysis estimates the effect of each prognostic factor considered alone without regard to coexisting prognostic factors. Table 3 summarizes the relative risk for patients by several factors using the likelihood ratio test of statistical significance. High stage and high pathologic grade indicated high relative risks but there were no statistically significant differences. Mucinous tumors were favorable and clear cell type were unfavorable with respect to overall survival in this study ($p=0{,}031$). However, the level of expression of HSP-60 was the most highly significant prognostic factor related to survival ($p=0.002$).

TABLE 3

| | Univariate analysis of survival time | | | |
|---|---|---|---|---|
| | P-value | | 95% confidence interval* | |
| Covariate | LLR test | Relative Risk | Lower limit | Upper limit |
| Age, yrs (N = 35)* | .284 | | | |
| Cell type (N = 51) | .031 | | | |
| serous | | 1.00 | | |
| mucinous | | 0.00185 | NS** | |
| endometrioid | | 4.11 | NS | |

TABLE 3-continued

| | Univariate analysis of survival time | | | |
|---|---|---|---|---|
| | P-value | | 95% confidence interval* | |
| Covariate | LLR test | Relative Risk | Lower limit | Upper limit |
| clear cell carcinoma | | 14.1 | 1.11 | 179 |
| adenocarcinoma, unspecified | | 3.55 | NS | |
| Path grade (N = 45) | .26 | | | |
| FIGO stage (N = 51) | .137 | | | |
| HSP level (N = 51) | .00176 | | | |
| low | | 1.00 | | |
| high | | 4.35 | 1.58 | 11.9 |

*Not significant if the interval includes the value of 1
**Not significant

Multivariate Analysis of Survival Time

Table 4 summarizes the relative death rates which were adjusted for the factors listed in the table. All patients were included in the estimates of the relative hazards except for six cases with missing information regarding pathologic grade. No significant correlation were evident between overall survival and cell type, pathologic grade, and FIGO stage in this study ($p>0.10$). After adjusting for these factors, it was estimated that those patients whose tumors had high HSP-60 expression experienced a 4.59-fold increase in their relative death rate when compared with those whose tumors had low HSP-60 mRNA expression ($p=0.012$).

TABLE 4

| | Multivariate analysis of survival time | | | |
|---|---|---|---|---|
| | | Relative | 95% confidence interval* | |
| Covariate | p-value | Risk | Lower limit | Upper limit |
| Cell type | .230 | | | |
| Pathologic grade | .174 | | | |
| FIGO stage | .717 | | | |
| HSP level | .012 | | | |
| low | | 1.00 | | |
| high | | 4.59 | 1.24 | 17.0 |

Overall Survival and HSP-60 mRNA Expression

FIG. 5 shows the relationship between HSP-60 mRNA expression and survival. Among the 25 patients in the low expression group (grade 1 or 2), 6 are dead of progressive disease and 19 were alive at the time of this analysis. In contrast, among the 26 patients in the high expression group (grade 3 or 4), 16 have died of progressive disease and 10 were alive. The median follow up is shown in Table 1. The median survival of the 25 patients in the low expression group was 46.8 months. The median survival of 26 patients in the high expression group was 22.1 months. Among the entire group of 51 patients in this study, patients in the high expression group had a significantly decreased overall survival rate (16% at 3.9 years) when compared with patients in the low expression group (41% at 4 years) as assessed by Kaplan-Meier survival analysis ($p=0.002$).

FIG. 6 shows the survival curves of the 44 patients with stage III tumors. The differences between the survival rate of the patients in the low expression group and the survival rate of the patients in the high expression group were also statistically significant in this subset ($p=0.001$). Similarly, survival analysis of the 38 patients in whom tumor samples were obtained prior to any chemotherapy (FIG. 7) also reveals a significantly worse survival in patients with high expression as compared with patients with low expression of HSP-60 ($p=0.004$). On the other hand, as shown in FIG. 5, no significant correlation between HSP-60 expression and overall survival was identified for the 13 patients in whom tumor samples were obtained at second or third look surgery after chemotherapy ($p=0.243$). FIG. 6 shows the effect on projected survival of HSP-P60 expression for the 41 patients documented to have grade 2 or 3 tumors, and indicates that a statistically significant effect of HSP-60 expression persists even when patients with low grade tumors are omitted from the analysis.

Southern Blot Analysis

Southern blot analysis of DNA digested by EcoR I showed no evidence of gene amplification or rearrangement. One major band of 3.5 Kb and three other minor bands were identified by the HSP-60 probe (FIG. 4).

Since Southern blot analysis showed no amplification of HSP-60 gene, the over-expression of HSP-60 mRNA observed in some tumors must result from the loss of normal regulatory mechanisms of transcription or degradation. Little is known about what factors other than heat can regulate HSP-60 expression. Recently, we have found that HSP-60 expression does not appear to be regulated by drugs and growth factors such as EGF, forskolin, and phorbol esters that can influence the phenotype and cisplatin sensitovarian cancer cells in culture (53).

The data presented here, which constitute the first report regarding HSP-60 and ovarian cancer, suggest that HSP-60 expression is a new prognostic factor for epithelial ovarian cancer and that the association of high HSP-60 levels with poor overall survival is independent of other prognostic factors.

A number of new and potentially valuable prognostic factors have emerged as a result of the recent technical advances in molecular genetics. Results of our investigations provide strong evidence that the level of HSP-60 mRNA expression is one of the valuable prognostic factors for epithelial ovarian cancer. Even in a population of patients too small for the known prognostic significance of grade and cell type to be readily identified, the significance of HSP-60 expression was easily discernible.

HSP-60 was first identified as a 58 kD heat shock protein (HSP-58) in Tetrahymena. HSP-58 was found in both non-heat-shocked as well as heat-shocked cells however, its concentration in the cell increased approximately two- to three-fold following heat shock, and this protein also accumulated specifically in mitochondria (45). The HSP-58 displays antigenic similarity with mitochondrially associated proteins from *Saccharomyces cerevisiae* (64 kD), *Xenopus laevis* (60 kD), and *Zea mays* (62 kD). Furthermore, a 58 kD protein from *Esch-*

*erichia coli* also exhibits antigenic cross-reactivity to an antiserum directed against the *T. thermophila* mitochondrial protein, and it is most likely the product of the well known groEL gene (46). On the other hand, a protein present in the stroma of higher plant chloroplasts, termed the Rubisco-binding protein, has been shown to have a sequence similar to the GroEL protein. The conservation and ubiquity of this class of proteins indicate that its specific roles in the assembly of Rubisco and of bacteriophage structural proteins reflect an essential cellular function, and these proteins have been called 'chaperonins' (47).

Increased synthesis of a 58 kD protein (a homolog of the bacterial groEL protein) was also observed in mammalian cells following exposure to elevated temperatures. The protein is present within the mitochondria of mammalian cells and it is not exposed on the cytoplasmic face of outer membrane (46). It is suspected that HSP-58, also referred as HSP-60, may function to facilitate the proper oligomeric assembly of proteins that are first synthesized in the cytoplasm and then translocated into the mitochondria. Recently, the cDNAs for HSP-60 from human (7), chinese hamster (13), and yeast (49) cells have been cloned and sequenced, and HSP-60 has also been identified as a microtubule-related protein (7).

Several clinicopathological prognostic factors of established significance, including age at diagnosis, cell type, FIGO stage, and extent of prior chemotherapy were equally distributed in the low and high HSP-60 mRNA expression groups; there was a small excess of grade 1 tumors in this low expression group. While no data was obtained on volume of the residual disease or performance status of the patients, it is unlikely that there were significant differences between the low expression group and the high expression group since 44 of the 51 patients (86%) had stage III tumor, there were no significant differences in stage between the low expression group and the high expression group, and furthermore all patients were treated at the same hospital according to the same regimen.

The two patients with stage IV and three patients with stage I were included in the low expression group and nineteen of the 44 patients with stage III (43.2%) were also included in the low expression group. This is interesting, because it has been previously reported that the HSP expression in tumor tissues correlates well with the clinical stage of the tumors, i.e., HSP-27 in breast cancer (36) and HSP-90 in ovarian cancer (31) Although the number of cases in this study is small, there is a possibility that HSP-60 expression may be a good prognostic factor for ovarian cancer independent of stage.

Many publications reporting prognostic factors for patients with epithelial ovarian tumors note that FIGO stage, pathologic grade, residual tumor size, ascites and cell type are the important factors. The current study was too small for either univariate or multivariate analyses of survival to identify any of these, except cell type ($p=0.031$), as statistically significant with respect to overall survival for the patients in this series. However, despite the limitation of size, this study shows that the effect of HSP-60 mRNA expression on overall survival was highly significant by both uni- and multivariate analyses ($p=0.00176$, and $p=0.012$) and that HSP-60 expression was an independent prognostic factor. The Kaplan-Meier survival curves for the 44 patients with stage III tumor indicate that the estimated survival rate of the patients in the high expression group is only 8.5% at 3.7 years which is worse than the survival rate reported for large numbers of such patients by FIGO (26% at 3 years, 17.2% at 5 years). Furthermore, the projected survival rate of the patients in the low expression group (41% at 3.9 years) is much better in comparison to the data of FIGO (42). Therefore, high level HSP-60 expression may allow the identification of a subset of ovarian cancer patients with poor prognosis in advanced stage.

The survival curves for patients without prior chemotherapy also showed significant differences as a function of HSP-60 mRNA expression (FIG. 4, $p=0.004$). Furthermore although not statistically significant because of the small number of patients, the survival of patients with prior chemotherapy was 37.9% for the low expression group and 15.3% for the high expression group (FIG. 6, $p=0.243$) at 3.5 years. Large studies are needed to determine whether HSP-60 expression is significant even in patients biopsied after chemotherapy. Also, the comparison of HSP-60 expression in samples before and after chemotherapy from the same patient will provide important information about the effect of chemotherapy on HSP-60 expression. HSP-60 is over-expressed in DDP-resistant ovarian cancer cell lines (52), and induced to low levels in DDP-sensitive ovarian cancer cell lines after exposure to DDP (53). Thus, there is a possibility that HSP-60 expression is directly related to the sensitivity of tumors to the platinum-containing drugs.

It is known that transcriptional activation of heat shock genes by increased temperature or other forms of cellular stress is mediated by the binding of a heat shock factor (HSF) to a conserved nucleotide sequence (the heat shock element) present in the promoter of heat-inducible genes (54). Many inducers of HSPs (i.e., ethanol, sodium arsenite, cadmium, anaerobiosis, recovery from anaerobiosis, etc.) are effective across a broad range of species (55). It was previously reported that human colon and testicular cancers have higher expression of HSP-60 mRNA than adjacent normal colonic or testicular tissue (49). HSP-60 expression was examined in three normal ovaries and five benign ovarian tumors (three serous adenoma and two mucinous adenoma). All these tissues showed low HSP-60 DNA expression (grade 1). It is currently not clear why some cancers express HSP-60 at higher levels than their normal tissues of origin, why there is such heterogeneity of expression among tumors of the same histologic type, or why expression is related to survival. There is a possibility that expression is regulated by hypoxia (47), and perhaps high level expression reflects tumor vascularization which in turn reflects rapid growth of tumor. According to this model, the less hypoxic environment in normal tissues, benign tumors, and malignant tumors with slow growth would result in a lower level of HSP-60. Since HSP-60 is an intrinsic mitochondrial protein (45), expression may reflect the numbers of mitochondria per cell, a parameter that may well vary with the biologic aggressiveness of the tumors.

Concluding Remarks

The foregoing description details specific methods that can be employed to practice the present invention. Having detailed those specific methods initially used to produce the present invention, the art-skilled will well enough know how to devise alternative reliable methods for arriving at the same information and for extending this information to other covered embodiments and related matters. Thus, however detailed the foregoing may appear in text, it should not be construed as limiting the overall scope hereof; rather, the ambit of the present invention is to be governed only by the lawful construction of the appended claims.

Bibliography

For the sake of convenience, reference shall be made herein to various publication by number enclosed within parantheses. These numbers correspond numerically to the citations grouped in the appended bibliography. By this means, we hereby expressly incorporate their contents into the present patent application.

1. Baker, G. H. *Brit J. Obstet. Gynecol.* 88:119 (1981).
2. Andrews, P. A. *Cancer Cells* 2:35 (1990).
3. Gottesman, M. M. *J. Biol. Chem.* 263:12163 (1988).
4. Andrews, P. A. *Cancer Comm.* 2:93 (1990).
5. Pruitt, S. C. *Gene* 66:121 (1988).
6. Isonishi, S. *J. Biol. Chem.* 265:3623 (1990).
7. Jindal, S. *Mol. Cell. Biol.* 9:2279 (1989).
8. Gupta, R. S. *J. Cell Biol.* 45:170 (1987).
9. Hoffman, W. *J. Mol. Biol.* 184:7132 (1985).
10. Hemmingsen, S. M. *Nature* (London) 33:330 (1988).
11. Shinnick, T. M., *J. Bacteriolo.* 169:1080 (1987).
12. Ellis, R. J. *Nature* (London) 328:378 (1987).
13. Picketts, D. J. *J. Biol. Chem.* 264:12001 (1989).
14. Andrews, P. A. *Proc. Am. Assoc. Cancer Res.* 31:378 (1990).
15. Gonais, S. L. *J. Biol. Chem.* 256:12478 (1981).
16. Gonias, S. L. *J. Biol. Chem.* 263:393 (1988).
17. Pizzo, S. V. *Biochem. J.* 238:217 (1986).
18. Kelly, S. L. *Science* 241:1813 (1988).
19. Gaudray, P. *J. Biol. Chem.* 261:6285 (1986).
20. Garnier, J. *J. Mol. Biol.* 1230:97 (1978).
21. Omura G A *J Clin Oncol* 9:1138 (1991).
22. Friedlander M L *Semin Oncol* 18: 205 (1991) .
23. Redman J R *J Clin Oncol* 4:513 (1986) .
24. Swenerton K D *Obstet Gynecol* 65:264 (1985).
25. Slamon D J *Science* 244:707 (1989).
26. Berchuck A *Cancer Res* 50:4087 (1991).
27. Morimoto R I In "Stress Proteins in Biology and Medicine" Cold Spring Harbor, Cold Spring Harbor Laboratory Press, pp 1–36 (1990).
28. Tandon A R *Proc Am Soc Clin Oncol* 9:23 (abstr) (1990).
29. Chamness G C *Proc Am Assoc Cancer Res* 30:252 (abstr) (1989).
30. Thor A *J Natl Cancer Inst* 83:170 (1991).
31. Mileo A M *Anticancer Res* 10:903 (1990).
32. Lunger T *Nature* 356:683 (1992).
33. Chirgwin J M *Biochemistry* 18:5294 (1979).
34. Slamon D J *Science* 244:707 (1989).
35. Slamon D J *Science* 224:256 (1984).
36. Thomas P S *Proc Natl Acad Sci USA* 77:5201 (1980).
37. Sambrook J In "Molecular Cloning, a Laboratory Manual (ed 2)" Cold Spring Harbor Laboratory press, pp 7.37–7.52 (1989).
38. Sambrook J In "Molecular Cloning, a Laboratory Manual (ed 2)" Cold Spring Harbor Laboratory Press, pp 10.13–10.17 (1989).
39. Sambrook J In "Molecular cloning, a Laboratory Manual (ed 2)" Cold Spring Harbor Laboratory Press, pp 9.24–9.58 (1989).
40. Lewontin R C *Biometrics* 21:19 (1965).
41. Cox D R *J R Stat Soc B* 34:187 (1972).
42. Bickel P J, Doksum K A: Mathematical Statistics: Basic Ideas and Selected Topics. Oakland, Calif., Holden-Day, Inc, (1977).
43. Kaplan E L *J Am Stat Assoc* 53:457 (1958).
44. Mantel N *J Stat Assoc* 58:690 (1963).
45. McMullin T W *Mol Cell Biol* 7:4414 (1987).
46. McMullin T W *Mol Cell Biol* 8:371 (1988).
47. Hemmingsen S M *Nature* 333:330 (1988).
48. Mizzen L A *J Biol Chem* 264:20664 (1989).
49. Reading D S *Nature* 337:655 (1989).
50. Kimura E *Proc Am Soc Clin Oncol* 10:101 (abstr) (1991).
51. Petterson F In "Annual report on the results of treatment in gynecological cancer" Vol 20, Stockholm, Sweden, International Federation of Gynecology and Obstetrics (1988).
52. Enns R E *Proc Am Assoc Cancer Res* 32:353 (abstr) (1991).
53. Kimura E *Proc Am Assoc Cancer Res* 33:362 (abstr) (1992).
54. Soger P K *Cell* 65:363 (1991).
55. Lindquist S *Ann Rev Biochem* 55:1151 (1986).

We claim:

1. A screening assay for determining an ovarian cancer patient's prognosis of survival with cis-platin treatment, said assay comprising the steps of:

a) measuring the levels of an expression product of an HSP-60 DNA molecule in 1) tumor cells of said patient and 2) control cells that are in normal tissue adjacent to said tumor cells, and b) determining the ratio of the level of expression in said tumor cells to the level of expression in said control cells; wherein a ratio less than about 2:1 indicates a good prognosis for survival with cis-platin treatment and a ratio greater than about 3:1 indicates a poor prognosis for survival with cis-platin treatment.

2. An assay according to claim 1 wherein said expression product is an HSP 60 polypeptide.

* * * * *